United States Patent
Barrus et al.

(10) Patent No.: US 8,814,919 B2
(45) Date of Patent: Aug. 26, 2014

(54) POSTERIOR PEDICLE SCREW HAVING A TAPER LOCK

(75) Inventors: Michael Barrus, Ashburn, VA (US); Jennifer Moore, Summit Point, WV (US)

(73) Assignee: K2M, Inc., Leesburg, VA (US)

( * ) Notice: Subject to any disclaimer, the term of this patent is extended or adjusted under 35 U.S.C. 154(b) by 265 days.

(21) Appl. No.: 12/739,461

(22) PCT Filed: Oct. 22, 2008

(86) PCT No.: PCT/US2008/080682
§ 371 (c)(1),
(2), (4) Date: Apr. 23, 2010

(87) PCT Pub. No.: WO2009/055407
PCT Pub. Date: Apr. 30, 2009

(65) Prior Publication Data
US 2010/0262196 A1    Oct. 14, 2010

Related U.S. Application Data

(60) Provisional application No. 61/000,071, filed on Oct. 23, 2007.

(51) Int. Cl.
*A61B 17/86* (2006.01)
(52) U.S. Cl.
USPC ........... 606/308; 606/305; 606/328; 606/266; 606/267
(58) Field of Classification Search
CPC ........... A61B 17/7032; A61B 17/7035; A61B 17/7037; A61B 17/86; A61B 17/8605; A61B 17/8685
USPC .................. 606/266–271, 305–308, 319, 328
See application file for complete search history.

(56) References Cited

U.S. PATENT DOCUMENTS

| | | | |
|---|---|---|---|
| 4,950,269 | A | 8/1990 | Gaines, Jr. |
| 5,683,392 | A | 11/1997 | Richelsoph et al. |
| 5,964,760 | A | 10/1999 | Richelsoph |
| 6,010,503 | A | 1/2000 | Richelsoph et al. |
| 6,280,442 | B1 | 8/2001 | Barker et al. |
| RE37,665 | E | 4/2002 | Ralph et al. |

(Continued)

FOREIGN PATENT DOCUMENTS

| | | |
|---|---|---|
| JP | 2005246061 A | 9/2005 |
| JP | 2007167642 A | 7/2007 |

OTHER PUBLICATIONS

International Search Report mailed Dec. 11, 2008 in counterpart International Application No. PCT/US08/80682 filed Oct. 22, 2008.

*Primary Examiner* — Eduardo C Robert
*Assistant Examiner* — Julianna N Harvey
(74) *Attorney, Agent, or Firm* — Carter, DeLuca, Farrell & Schmidt, LLP (57) ABSTRACT

A pedicle screw construct includes a pedicle screw, a coupling, and a collet. The pedicle screw includes a shank having a helical thread formed thereon and a head at one end. The collet is positioned atop the head of the pedicle screw. The collet and pedicle screw are inserted into the coupling. The pedicle screw is rotatable and pivotable relative to the collet and coupling assembly. The collet and the coupling each have a saddle that is adapted and configured for receiving a rod member.

19 Claims, 7 Drawing Sheets

(56) References Cited

U.S. PATENT DOCUMENTS

| | | |
|---|---|---|
| 6,413,258 B1 | 7/2002 | Bernhardt, Jr. |
| 6,660,004 B2 | 12/2003 | Barker et al. |
| 6,736,820 B2 | 5/2004 | Biedermann et al. |
| 6,974,460 B2 | 12/2005 | Carbone et al. |
| RE39,089 E | 5/2006 | Ralph et al. |
| 7,087,057 B2 * | 8/2006 | Konieczynski et al. ...... 606/278 |
| 7,090,674 B2 | 8/2006 | Doubler et al. |
| 7,105,029 B2 | 9/2006 | Doubler et al. |
| 7,118,303 B2 | 10/2006 | Doubler et al. |
| 7,334,961 B2 | 2/2008 | Doubler et al. |
| 7,335,201 B2 | 2/2008 | Doubler et al. |
| 7,445,627 B2 | 11/2008 | Hawkes et al. |
| 7,658,582 B2 | 2/2010 | Doubler et al. |
| 7,678,136 B2 | 3/2010 | Doubler et al. |
| 2005/0053423 A1 | 3/2005 | Doubler et al. |
| 2005/0080415 A1* | 4/2005 | Keyer et al. ...................... 606/61 |
| 2005/0203516 A1* | 9/2005 | Biedermann et al. ........... 606/61 |
| 2006/0161153 A1 | 7/2006 | Hawkes et al. |
| 2006/0173456 A1 | 8/2006 | Hawkes et al. |
| 2006/0276792 A1* | 12/2006 | Ensign et al. ................... 606/61 |
| 2007/0093817 A1 | 4/2007 | Barrus et al. |
| 2007/0286703 A1 | 12/2007 | Doubler et al. |
| 2008/0137933 A1 | 6/2008 | Kim |
| 2008/0243193 A1* | 10/2008 | Ensign et al. ................. 606/305 |

* cited by examiner

POSTERIOR PEDICLE SCREW HAVING A TAPER LOCK

CROSS-REFERENCE TO RELATED APPLICATIONS

The present application is a National Stage Entry of PCT/US2008/080682, which was filed Oct. 22, 2008, and claims priority to U.S. Provisional Application No. 61/000,071 filed Oct. 23, 2007, the contents of which are incorporated herein by reference.

BACKGROUND

1. Technical Field

The present disclosure relates to pedicle screws and, more particularly, to a posterior pedicle screw having a taper lock.

2. Background of Related Art

The human spine is the supporting axis of the body and makes all the movement of a person's head, arms, and legs possible. It is a highly flexible structure, capable of a high degree of curvature and twist in nearly every direction. An adult spine generally has twenty-four vertebrae, which can be categorized into three major sections. These categories include the cervical spine, the thoracic spine, and the lumbar spine. The cervical spine is composed of the upper seven vertebrae, the thoracic spine is composed of the next twelve vertebrae, and the lumbar spine is composed of the final five vertebrae. Below the lumbar spine is a bone called the sacrum, which is part of the pelvis. Muscles and ligaments are attached to a slender projection from the back of the vertebrae known as the spinous process. Housed within a narrow channel in the center of spine is the spinal cord. All the nerves of the body are connected to the spinal cord.

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

Depending upon how such systems are coupled to the spine, the systems may be classified as anterior, posterior, or lateral implants. For example, lateral and anterior systems are coupled to the anterior portion of the spine. Posterior systems generally comprise a pair of rods that are fixed to adjacent vertebrae with pedicle screws or hooks on either side of the spinous process along a section of the spine. Achieving the optimum alignment of a system with the vertebrae to which it is to be coupled is limited by the range of motion achievable by the system, i.e., the greater the range of motion achievable by the assembly, the more closely aligned the assembly may be with the vertebrae. In addition to the limited range of motion achievable by current systems, currently available systems are often complex, unreliable, and difficult to manipulate.

SUMMARY

A pedicle screw construct is presently disclosed. The pedicle screw construct includes a coupling having an opening extending therethrough, a collet receivable in the opening of the coupling, and a pedicle screw having a head receivable in an opening of the collet, the pedicle screw including a shank, a head having a top and a bottom surface, and a neck between the bottom of the head and the shank, the head receivable in an opening of the collet, such that the pedicle screw is movable, throughout a plurality of positions, substantially free from interference between the neck and the collet and between the neck and the coupling. The pedicle screw is movable in a cone with a range of movement that is between about 70° and about 95°.

The collet may further include a bottom edge having an annular beveled lip extending upwards and inwards from the bottom outer edge of the collet, and the coupling may further include a bottom edge having an annular beveled lip extending upwards and inwards from the bottom outer edge of the coupling.

The shank may further include a helical thread formed thereon. The neck may have a diameter that is less than a diameter of the bottom of the head or a diameter of the helical thread of the shank.

The coupling may further include a plurality of fingers on opposing regions of the coupling defining a saddle having a generally U-shaped configuration. The collet may further include a plurality of wings, each defining a longitudinal axis, on opposing regions of the collet defining a saddle having a generally U-shaped configuration defining a nadir.

A slot may extend from the nadir of the collet towards the bottom portion of the collet. At least one groove may extend substantially perpendicular to the longitudinal axis of at least one wing, defining front and rear portions of the collet. The collet may further include a notch opening at the bottom of the collet and extends substantially perpendicular to the longitudinal axis of at least one wing.

BRIEF DESCRIPTION OF THE DRAWINGS

Embodiments of the presently disclosed posterior pedicle screw having a taper lock are described herein with reference to the accompanying drawings, wherein.

DETAILED DESCRIPTION OF THE EMBODIMENTS

Embodiments of the presently disclosed pedicle screw having a posterior taper lock will now be described in detail with reference to the drawing figures wherein like reference numerals identify similar or identical elements. In the drawings and in the description which follows, the term "proximal", as is traditional, will refer to the end of the pedicle screw which is closest to the operator while the term "distal" will refer to the end of the pedicle screw which is furthest from the operator.

Figure 1A:
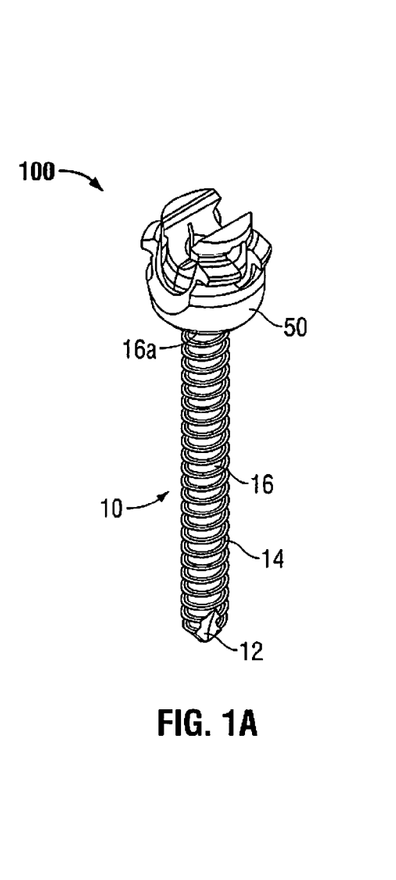
FIG. 1A is a top perspective view of the presently disclosed pedicle screw having a taper lock.
Figure 1B:
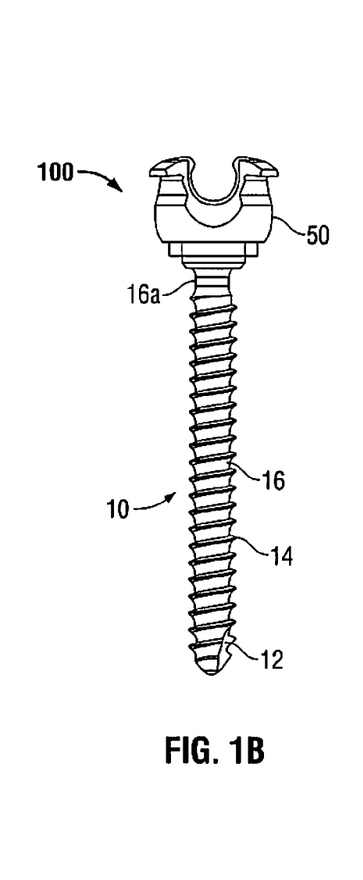
FIG. 1B is a front view of the pedicle screw of FIG. 1A.
Figure 1C:
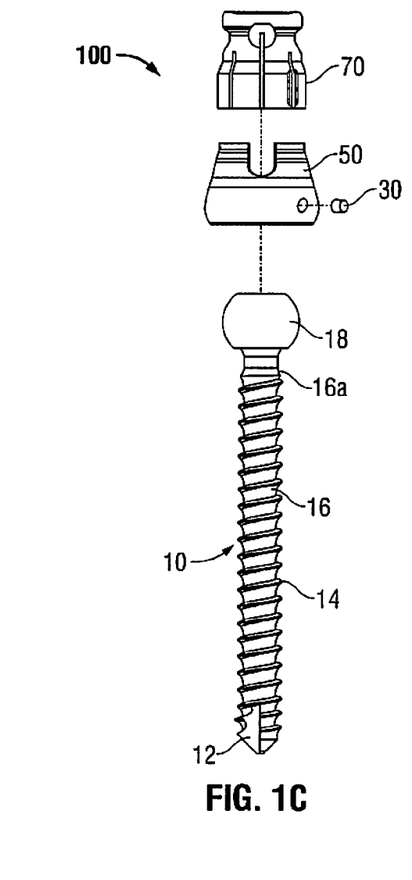
FIG. 1C is an exploded side view of the pedicle screw of FIG. 1A with parts separated illustrating a pedicle screw, a coupling, a collet, and a pin.

Referring initially to FIGS. 1A-1C, in which like reference numerals identify similar or identical elements, a pedicle screw construct is generally designated as 100. The pedicle screw construct 100 includes a pedicle screw 10, a pin 30, an outer housing or coupling 50, and an inner housing or collet 70.

Figure 2A:
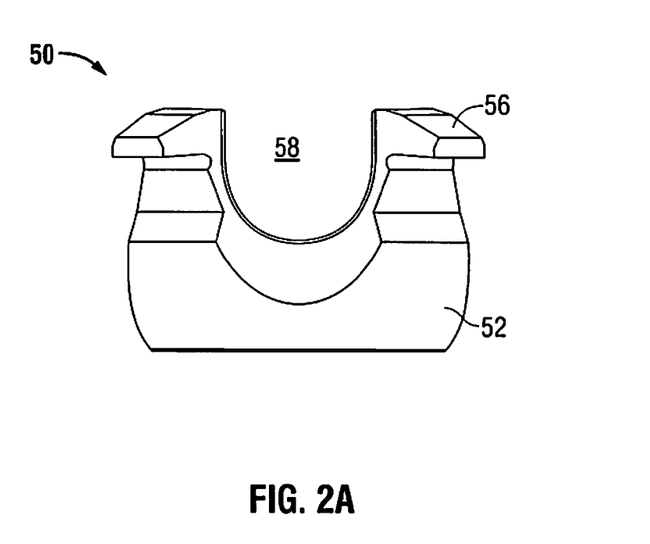
FIG. 2A is a front view of the coupling.
Figure 2B:
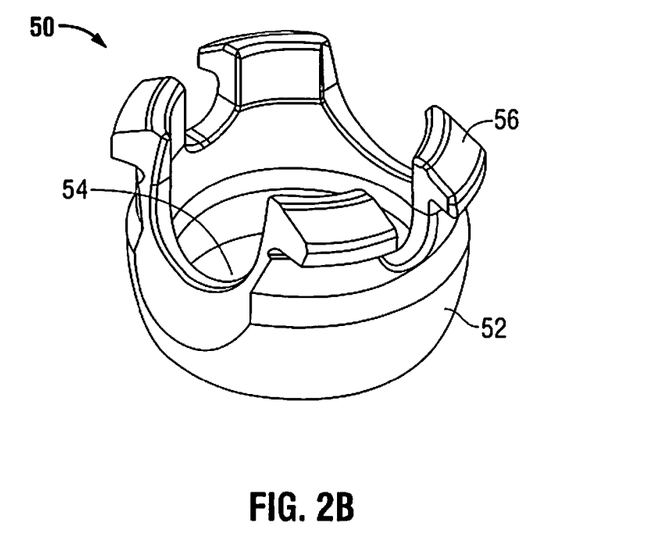
FIG. 2B is a top perspective view of the coupling of FIG. 2A.

Referring now to FIGS. 2A and 2B, the coupling 50 includes an annular body portion 52 having an opening 54 extending axially therethrough. Additionally, the coupling 50 includes a plurality of fingers 56 that are located in opposing regions of the coupling 50 and define a saddle 58 having a generally U-shaped configuration. The u-shaped saddle 58 is configured and dimensioned for receiving a rod (not shown).

Figure 3A:
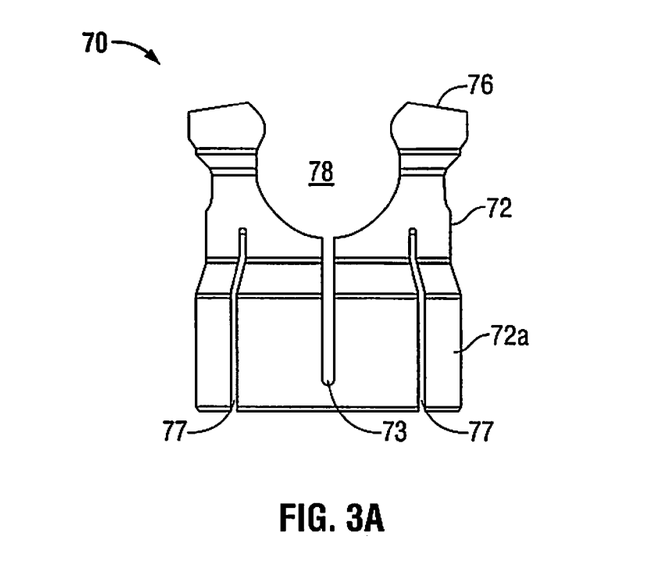
FIG. 3A is a front view of the collet.
Figure 3B:
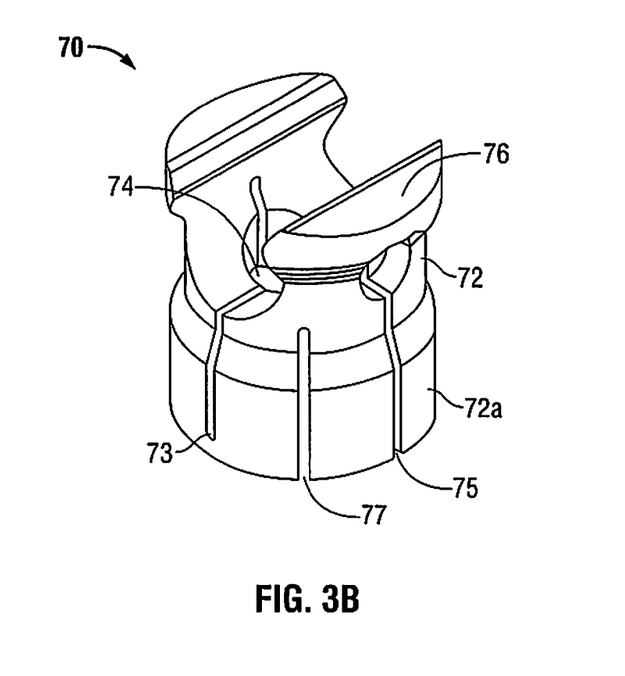
FIG. 3B is a top perspective view of the collet of FIG. 3A.

As shown in FIGS. 3A and 3B, the collet 70 has a generally cylindrical body portion 72 with an opening 74 extending axially therethrough. A pair of upstanding wings 76 defines a saddle 78 having a generally U-shaped configuration. The saddle 78 is configured and dimensioned for receiving a rod (not shown). The body portion 72 includes a slot 73 that extends from the nadir of the saddle 78 towards the bottom of the body portion 72 and essentially bisects the body portion 72 along a central axis, and defines left and right sections of the body portion as viewed in FIG. 3A. Preferably, the slot does not extend all the way through the body portion. Although less desirable, such a full slot could be used. This arrangement permits each of the wings 76 to flex towards and away from each other. The dimensions of the saddle 78 vary according to the flexure of the wings 76. As the wings 76 are moved closer to each other, the saddle 78 decreases in size and when the wings 76 are moved away from each other, the saddle 78 increases in size. Allowing the saddle 78 to vary in size permits the collet 70 to accommodate rods (not shown) having differing outside diameters. Alternatively, compressing the wings 76 towards each other increasingly engages the outer surface of a rod located in the saddle 78, thereby frictionally securing the rod in a desired position.

In addition, the body portion includes a plurality of grooves 75 that extend to the bottom of the body portion 72 and which are open at the bottom of the body portion 72. The grooves 75 extend vertically into each of the wings 76, and define front and rear portions of the body portion 72. As configured, the grooves 75 permit the front and rear sections of the body portion 72 to flex relative to the grooves 75 along the axis defined by the slot 73. The body portion 72 also includes a plurality of notches 77 that are open at the bottom surface of the body portion 72 and extend vertically towards the wings 76. The notches 77, in combination with the slot 73 and the grooves 75, allow arcuate sections 72a of the body portion 72 to flex inwards and outwards from an initial position in response to compressive and tensile forces applied to the sections 72a.

Figure 4A:
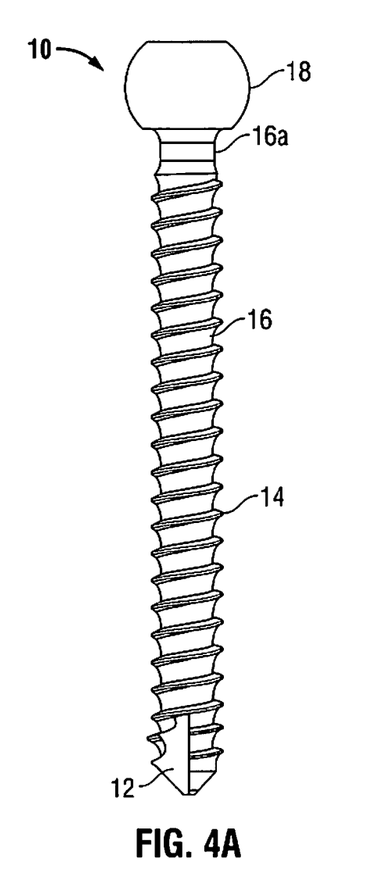
FIG. 4A is a side view of the pedicle screw.
Figure 4B:
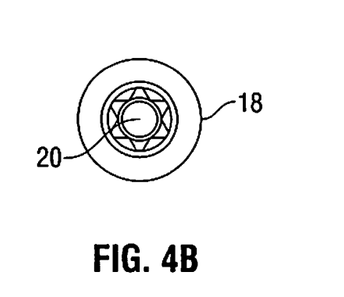
FIG. 4B is a top view of the pedicle screw of FIG. 4.
Figure 5:
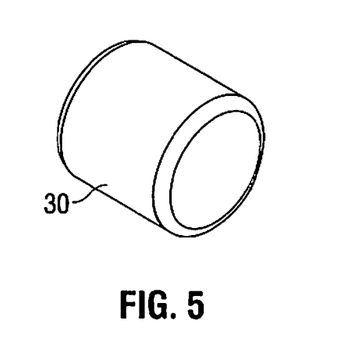
FIG. 5 is a front perspective view of the pin.

Referring now to FIGS. 4A and 4B, the pedicle screw 10 includes a shank 16 having a helical thread 14 formed thereon. A cutting portion 12 is formed at a distal end of the pedicle screw 10. A head 18 is located at a proximal end of the pedicle screw 10. The head 18 includes a plurality of grooves 36 formed thereon and has an outer diameter that is greater than the outer diameter of the shank 16. On the top surface of the head 18, a recess 20 is formed. The recess 20 is illustrated with a six-pointed star configuration for receiving the operative end of a suitable driving tool, but it is contemplated that other configurations may be used. A neck 16a extends between a bottom surface of the head 18 and the beginning of the helical thread 14. As configured, the neck 16a is unthreaded. As shown, at least a portion of the diameter of the neck 16a is less than the diameter of the bottom of the head 18 and the major diameter of the threaded portion of the shank 16.

Referring again to FIGS. 1A-1C, the pedicle screw construct 100 will now be discussed as assembled for use. The collet 70 is seated atop the head 18 of pedicle screw 10. The opening at the bottom of collet 70 is dimensioned and configured for receiving the head 18. As such, the collet 70 and the head 18 are rotatable and pivotable in relation to each other, thereby allowing the pedicle screw 10 to be repositioned in a plurality of orientations relative to the collet 70. The combination of the collet 70 and pedicle screw 10 is inserted into the coupling 50. The pin 30 aligns the collet 70 and the coupling 50 for maintaining a fixed relationship between them. As assembled, the pedicle screw 10 is rotatable and pivotable in relation to the collet 70 and the coupling 50 as will be discussed in further detail hereinbelow.

Figure 6:
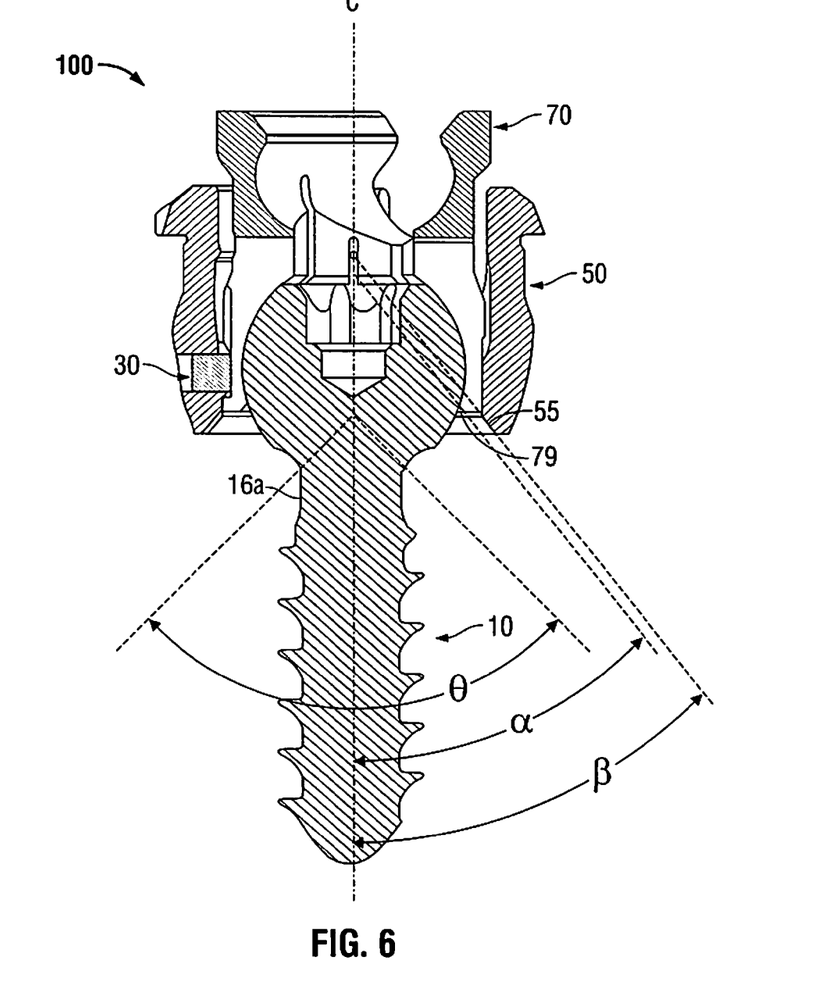
FIG. 6 is a side cross-sectional view of the pedicle screw of FIG. 1A.

Referring now to FIG. 6, additional features of the assembled pedicle screw construct 100 will be discussed. The coupling 50 includes an inner annular lip 55 that is beveled. The lip 55 extends upwards and inwards from a bottom outer edge of the coupling 50. Additionally, the collet 70 includes an annular beveled lip 79 that also extends upwards and inwards from bottom outer edge of the collet 70. As shown in FIG. 6, angle α measures the angle of the beveled lip 79 from centerline C to the beveled lip 79. Angle α may measure between 25 and 65 degrees. In an embodiment, angle α is approximately equal to 45 degrees. Angle β measures the angle of the beveled lip 55 from the centerline C to the beveled lip 55. Angle β may measure between 32 and 72 degrees. In an embodiment, angle β is approximately equal to 52 degrees. By providing the coupling 50 and the collet 70 with beveled lips 55, 79, there is a reduced interaction between the head 18 and the coupling 50 and/or the collet 70. In addition, the pedicle screw 10 has a neck 16a with a length and diameter that cooperate with the beveled lips 55, 79 for reducing interaction therebetween. That is, the length of the non-threaded neck portion 16a of the pedicle screw 10 extends a distance from the bottom of the head 18 to a point beyond the beveled lip 79 of the of the collet 70 and beveled lip 55 of the coupling 50, which together with the selected diameter of the neck 16a permits maximum angular motion of the pedicle screw 10 relative to the collet 70 and coupling 50. This creates a smooth transition zone between the unthreaded neck 16a and the collet 70 and the coupling 50. By reducing the interference between the neck 16a and the beveled lips 55, 79 in combination with the reduced interaction between the head 18 and the beveled lips 55, 79, the pedicle screw 10 defines a cone of at least 70° with respect to a centerline "C" of the pedicle screw construct (FIG. 6). In another embodiment, the pedicle screw 10 has a conical range of motion that is at least 90°. In a further embodiment, the pedicle screw 10 has a conical range of motion that is at least 95°.

Specifically, the pedicle screw 10 is capable of being repositioned from a first position (FIG. 6) throughout a plurality of angular positions with respect to the centerline "C". The angular displacement with respect to the centerline "C" is shown as angle θ. Angle θ is at least 70°. In other embodiments, angle θ is in a range between about 80° and about 95°. As such, the pedicle screw 10 moves relative to the centerline "C" (i.e. off axis) in a range of about 35° to about 47.5°.

Figure 7:
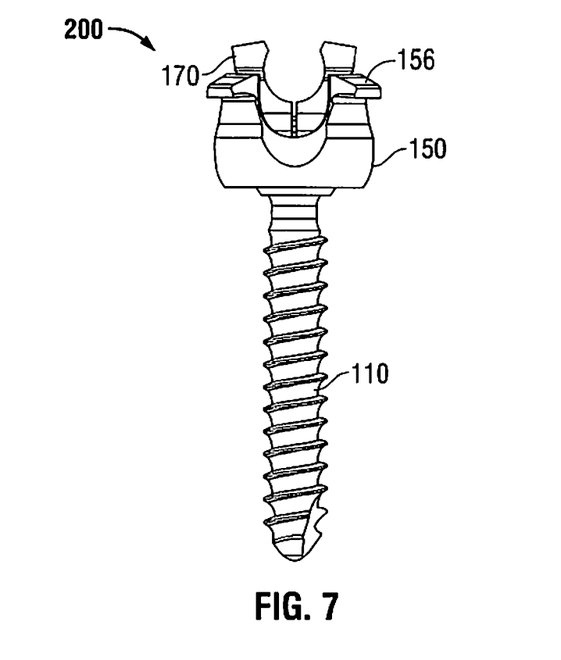
FIG. 7 is a front view of a pedicle screw according to another embodiment of the present disclosure.
Figure 8A:
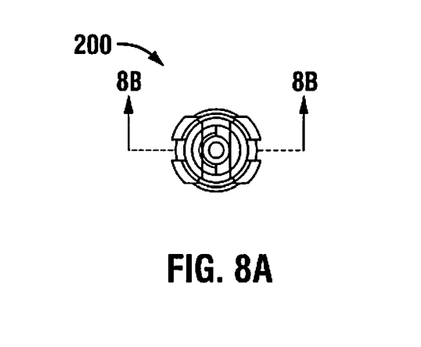
FIG. 8A is a top view of the pedicle screw of FIG. 7.
Figure 8B:
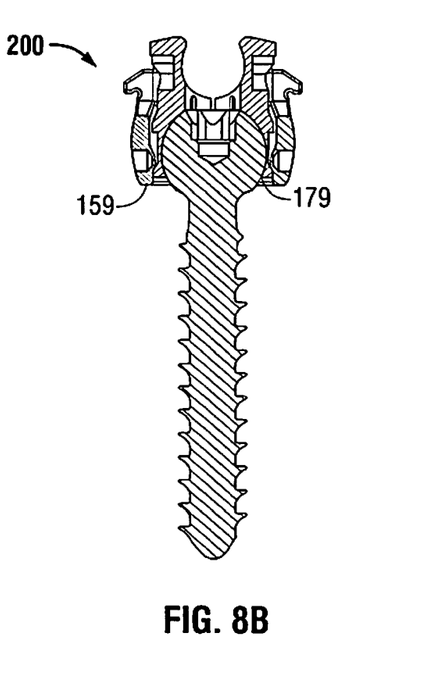
FIG. 8B is a cross-sectional view of the pedicle screw of FIG. 7 taken along section line A-A.
Figure 9:
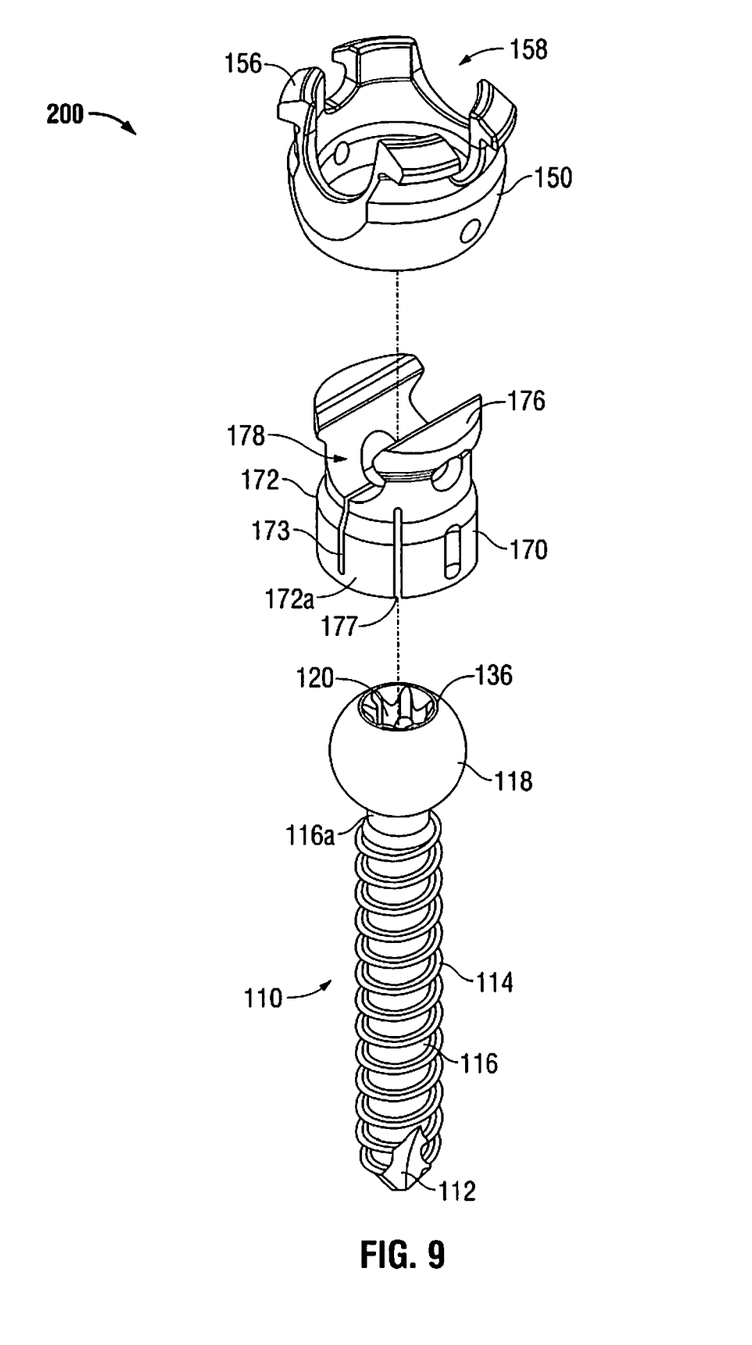
FIG. 9 is an exploded view of the pedicle screw of FIG. 7.

An alternate embodiment of a pedicle screw construct 200 is shown in FIGS. 7 to 9. In this embodiment, pedicle screw construct 200 does not include the pin 30 that was included in pedicle screw construct 100 (FIG. 1C). The pedicle screw construct 200 is discussed in greater detail below.

As shown in FIG. 9, a pedicle screw construct 200 includes an outer housing or coupling 150, an inner housing or collet 170, and a pedicle screw 110. When assembled, as shown in FIG. 7, the pedicle screw 110 is rotatable and pivotable in relation to the collet 170 and the coupling 150.

The coupling 150 includes a plurality of fingers 156 that are located in opposing regions of the coupling 150 and define a saddle 158 having a generally U-shaped configuration. The U-shaped saddle 158 is configured and dimensioned for receiving a rod (not shown).

The collet 170 has a generally cylindrical body portion 172 with an opening 174 extending axially therethrough. A saddle 178 having a generally U-shaped configuration for receiving a rod (not shown) is defined by a pair of upstanding wings 176. A body portion 172 includes a slot 173 extending from the nadir of the saddle 178 towards the bottom of the body portion 172 and essentially bisects the body portion 172 along a central axis. Preferably, although not necessarily, slot 173 would not extend all the way through the body portion. This arrangement allows the wings 176 to flex away and towards each other allowing saddle 178 to accommodate rods (not shown) of various sizes. Notches 177 in combination with slot 173 allow arcuate sections 172a of the body portion 172 to flex inwards and outwards.

Referring now to FIGS. 7 and 9, in one embodiment, the pedicle screw 110 includes a shank 116 having helical thread 114 formed thereon. In an embodiment, a head 118 located at a proximal end of the pedicle screw 110 includes a plurality of grooves 136 and a recess 120 is formed on the head 118 for receiving the operative end of a suitable driving tool. A cutting portion 112 is formed at a distal end of the pedicle screw 110. A neck 116a extends between a bottom surface of the head 118 and the beginning of the helical thread 114. As configured, the neck 116a is unthreaded and at least a portion of the diameter of the neck 116a is less than the diameter of the bottom of the head 118 and the major diameter of the threaded shank 116.

As shown in FIG. 8A, the coupling 150 has an inner annular lip 155 that is beveled. The lip 155 extends upwards and inwards from a bottom edge of the coupling 150. Additionally, the collet 170 includes an annular beveled lip 179 that also extends upwards and inwards from the bottom edge of the collet 170. The beveled lips 155, 179, reduce the interaction between the head 118 and the coupling 150 and/or the collet 170. The neck 116a of the pedicle screw 110 cooperates with the beveled lips 155, 179, to reduce interaction and increase the range of included conical angulation.

The presently disclosed pedicle screw construct 100, 200 is adaptable for spinal procedures. In particular, the pedicle screw construct 100, 200 includes a relatively short pedicle screw 10, which is suitable for procedures in the cervical region of the spine, since the forces and/or stresses applied to the pedicle screw 10 in the cervical region are lower than those of either the lumbar or the thoracic regions. It is contemplated that beveling the inner surfaces of the coupling and the collet in a pedicle screw construct for use in the thoracic or lumbar regions would increase their angular range of movement.

While the foregoing description contemplates the use of a preferred design of taper lock screw, which provides advantages particularly when used in the areas of the spine such as the cervical spine where the amount of soft tissue covering the spine is less than in other regions of the spine. It is contemplated that a screw having increased angulation between the screw and the rod coupling housing can be achieved with other designs of screws. By way of example only, it is believed that incorporation of a bevel in the housing of the structure disclosed in U.S. Pat. Nos. 6,280,442 and 6,660,004 in combination with a screw having a neck with correspondingly adjusted neck diameter and neck length may achieve some or all of the advantages of the structure described herein. In addition, it is also contemplated that the advantages of the structures described herein could be achieved in screw constructions as shown in U.S. Publications 2006/0161153 and 2006/0276792.

It will be understood that various modifications may be made to the embodiments of the presently disclosed pedicle screw construct. Therefore, the above description should not be construed as limiting, but merely as exemplifications of embodiments. Those skilled in the art will envision other modifications within the scope and spirit of the present disclosure.

What is claimed is:

1. A taper lock bone screw comprising:
    a coupling having an inner surface, the inner surface defining a first opening that extends through the coupling, the inner surface having a first annular beveled lip that extends upwards and inwards proximally and inwardly from a bottom edge of the coupling;
    a collet having an inner surface and receivable in the first opening of the coupling, the inner surface of the collet defining a second opening having a second annular beveled lip that extends proximally and inwardly from a bottom edge of the collet, the collet defining a U-shaped saddle in a proximal end of the collet, the U-shaped saddle dimensioned to receive a rod, the collet being in contact with the coupling in a taper lock arrangement to secure the rod to at least one of the coupling and the collet such that the coupling is movable relative to the collet in a proximal direction toward the proximal end of the collet when the rod is received in the U-shaped saddle of the collet, wherein proximal movement of the coupling relative to the collet locks the rod within the U-shaped saddle of the collet; and
    a pedicle screw including a shank, a head having a top and a bottom surface, and a neck between the bottom surface of the head and the shank, the head receivable in the second opening of the collet, such that the pedicle screw is movable throughout a plurality of positions and is substantially free from interference between the neck and the collet and between the neck and the coupling, the head contacting the inner surface of the collet when the head is received in the second opening of the collet.

2. The taper lock bone screw of claim 1, wherein the pedicle screw has a conical range of motion of at least 70 degrees.

3. The taper lock bone screw of claim 1, wherein
    an angle is defined between the first annular beveled lip of the coupling and a centerline of the pedicle screw, the angle having a value between 32 and 72 degrees, and
    a second angle is defined between the second annular beveled lip of the collet and the centerline of the pedicle screw, the second angle having a value between 25 and 65 degrees.

4. The taper lock bone screw of claim 1, wherein
    the shank includes a helical thread formed thereon; and
    the neck has a diameter that is less than a diameter of the bottom surface of the head or a diameter of the helical thread of the shank.

5. The taper lock bone screw of claim 1, wherein
    the coupling has a U-shaped configuration including a plurality of fingers on opposing regions of the U shaped configuration; and the U-shaped saddle of the collet has a plurality of wings, each wing of the plurality of wings defining a longitudinal axis such that longitudinal axes of the plurality of wings are on opposing regions of the collet, the U-shaped saddle defining a nadir.

6. The taper lock bone screw of claim 5, wherein at least one slot extends from the nadir of the U-shaped saddle towards a bottom portion of the collet.

7. The taper lock bone screw of claim 5, wherein the collet defines at least one groove that extends substantially perpendicular to the longitudinal axis of at least one wing of the plurality of wings, the at least one groove defining front and rear portions of the collet.

8. The taper lock bone screw of claim 5, wherein the collet defines at least one notch that is open at a bottom portion of the collet and extends substantially perpendicular to the longitudinal axis of at least one wing of the plurality of wings.

9. The taper lock bone screw of claim 5, wherein the collet defines at least one groove that extends from the nadir of the U shaped saddle towards a bottom portion of the collet.

10. The taper lock bone screw of claim 5, wherein the plurality of wings are adapted and configured to flex towards and away from one another.

11. The taper lock bone screw of claim 5, wherein the size of the U-shaped saddle of the collet is adjustable by flexing the plurality of wings toward or away from one another.

12. The taper lock bone screw of claim 5, wherein the U-shaped saddle of the collet is configured and adapted to frictionally secure the rod therein.

13. The taper lock bone screw of claim 1, wherein the first and second annular beveled lips are disposed axially adjacent to each other along a longitudinal axis defined through proximal and distal ends of the taper lock bone screw to increase maximum angular orientation of the pedicle screw relative to the longitudinal axis when the pedicle screw is moved relative to the coupling and the collet.

14. The taper lock bone screw of claim 13, wherein the pedicle screw has a conical range of motion of at least 70 degrees with respect to a centerline of the pedicle screw.

15. The taper lock bone screw of claim 14, wherein the conical range of motion of the pedicle screw is at least 90 degrees with respect to the centerline of the pedicle screw.

16. The taper lock bone screw of claim 15, wherein the conical range of motion of the pedicle screw is at least 95 degrees with respect to the centerline of the pedicle screw.

17. The taper lock bone screw of claim 13, wherein the pedicle screw moves in a range of about 35 degrees to about 47.5 degrees relative to a centerline of the pedicle screw.

18. The taper lock bone screw of claim 1, wherein the collet is integrally formed.

19. The taper lock bone screw of claim 1, wherein the U-shaped saddle is positioned on a proximal end portion of the collet and the second opening of the collet is defined on a distal end portion of the collet, the coupling being axially movable relative to both the proximal and distal end portions of the collet when the rod is received within the U-shaped saddle of the collet.

* * * * *